United States Patent
Shukla et al.

(10) Patent No.: US 7,427,659 B2
(45) Date of Patent: Sep. 23, 2008

(54) PROCESS FOR PURIFYING PROTEINS IN A HYDROPHOBIC INTERACTION CHROMATOGRAPHY FLOW-THROUGH FRACTION

(75) Inventors: Abhinav A. Shukla, Bellevue, WA (US); Sanchayita Ghose, Newcastle, WA (US)

(73) Assignee: Amgen Inc., Thousand Oaks, CA (US)

( * ) Notice: Subject to any disclaimer, the term of this patent is extended or adjusted under 35 U.S.C. 154(b) by 144 days.

(21) Appl. No.: 10/970,860

(22) Filed: Oct. 22, 2004

(65) Prior Publication Data

US 2005/0136521 A1    Jun. 23, 2005

Related U.S. Application Data

(60) Provisional application No. 60/514,486, filed on Oct. 24, 2003.

(51) Int. Cl.
*C07K 1/00* (2006.01)
*C07K 14/00* (2006.01)

(52) U.S. Cl. .................. 530/350; 530/344; 530/412; 435/69.1; 435/7.1; 435/183; 435/325

(58) Field of Classification Search ............ 530/350, 530/344, 412; 435/69.1, 7.1, 183, 325
See application file for complete search history.

(56) References Cited

U.S. PATENT DOCUMENTS

| | | | | |
|---|---|---|---|---|
| 5,463,029 | A | * | 10/1995 | Dunn et al. ............... 530/416 |
| 5,641,870 | A | * | 6/1997 | Rinderknecht et al. ...... 530/417 |
| 6,005,082 | A | * | 12/1999 | Smeds ..................... 530/417 |
| 2003/0009025 | A1 | | 1/2003 | Smith et al. |
| 2005/0136521 | A1* | | 6/2005 | Shukla et al. ............. 435/183 |

FOREIGN PATENT DOCUMENTS

| | | |
|---|---|---|
| JP | 04-049299 A | 2/1992 |
| WO | WO 95/22389 A1 | 8/1995 |
| WO | WO 96/33208 A1 | 10/1996 |
| WO | WO 00/59927 A1 | 10/2000 |
| WO | WO 01/72769 A3 | 10/2001 |

OTHER PUBLICATIONS

Schoel et al. , J. Chromatography 587, 19-23 (1991).*
Amersham Pharmacia Biotech catalog (1998) p. 229.*
Danielsson et al. , J. Immunological Methods 115, 79-88 (1988).*
Crupper, Scott S., et al., "Exploiting the Unique Biophysical Properties of Bacteriocins to Purify Bac1829 from *Staphylococcus aureus* KSI1829," 9 *Protein Expression and Purification* 228-232 (1997).
Schoel, Bernd, et al., "Hydrophobic interaction chromatography for the purification of cytolytic bacterial toxins," 667(1-2) *J Chromatogr. A* 131-139 (1994).
Shansky, et al., "Hydrophobic Interaction Chromatography of Biopolymers," in *HPLC of Biological Macromolecules: Methods and Applications* (ed. by Gooding, K.M. and Regnier, F.E.), p. 117, 1990.

* cited by examiner

*Primary Examiner*—Chih-Min Kam
(74) *Attorney, Agent, or Firm*—Christopher L. Wight; Brinks Hofer Gilson & Lione; Kathleen Fowler

(57) ABSTRACT

The present invention is a process for separating a target protein (such as a recombinant protein produced in a cell culture) from a mixture containing the target protein and contaminants (such as cell culture contaminants), by contacting the mixture with a hydrophobic adsorbent comprising branched hydrocarbon functional groups in an aqueous salt solution and collecting the unbound flow-through fraction containing the target protein. In one embodiment, the hydrophobic adsorbent may be a branched alkyl functional group. In another embodiment, the branched alkyl functional group has from 3 to 8 carbon atoms. In another embodiment, the branched alkyl functional group is a tertiary carbon atom, such as tert-butyl.

12 Claims, 4 Drawing Sheets

| | |
|---|---|
| Column: | Macroprep t-butyl 10.00mmD/ 55n |
| Sample: | -- None -- |
| Flow Rate: | 2.00 ml/min. |
| Wavelength: | 1: 280 nm |

| | |
|---|---|
| Elution: | |
| Step | 100% A:400nM Citr in 3.00 CV |
| Step | 100% C:H2O in 4.00 CV |
| Step | 100% C:H2O in 4.00 CV |

Fig. 4
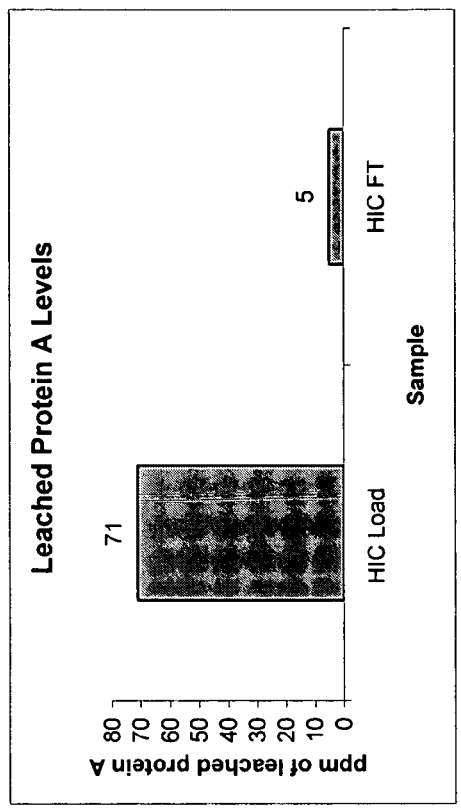
Fig. 4a
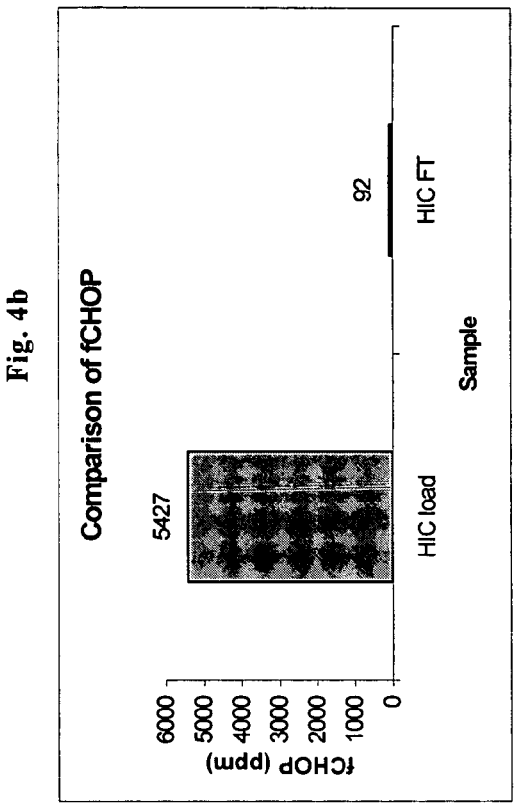
Fig. 4b
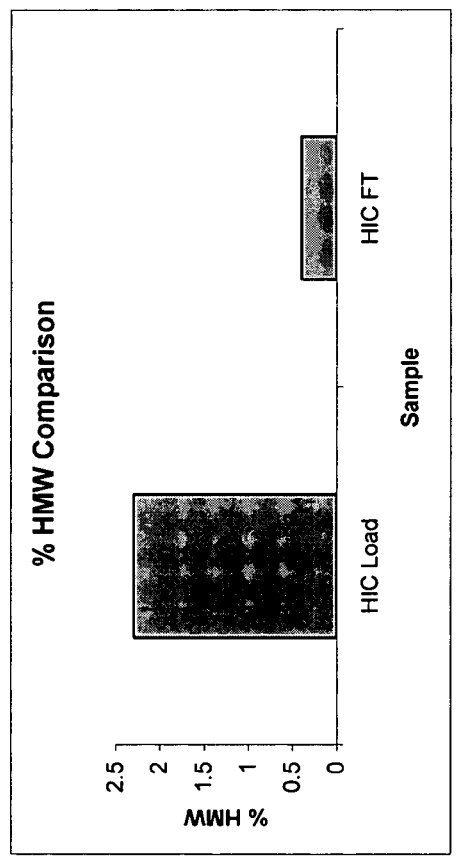
Fig. 4c
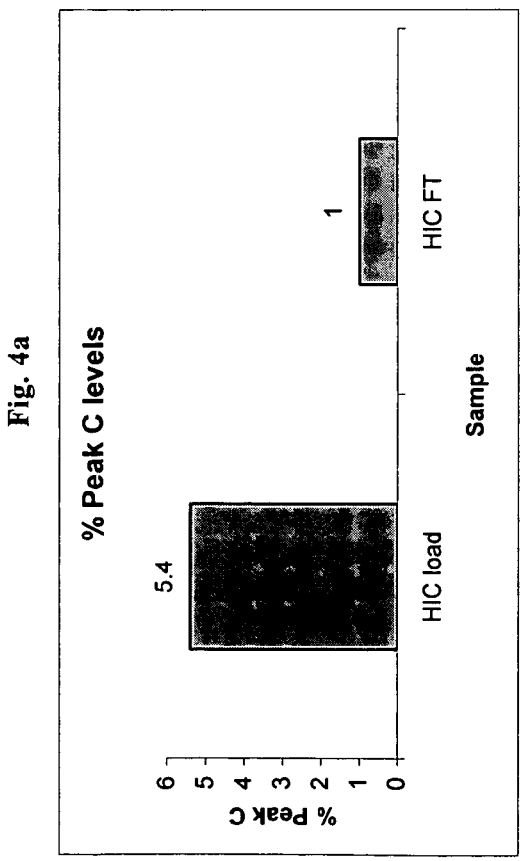
Fig. 4d

PROCESS FOR PURIFYING PROTEINS IN A HYDROPHOBIC INTERACTION CHROMATOGRAPHY FLOW-THROUGH FRACTION

CROSS-REFERENCE TO RELATED APPLICATION

This application claims the benefit of the filing date of U.S. Provisional Patent Application Ser. No. 60/514,486, filed Oct. 24, 2003.

FIELD OF THE INVENTION

The present invention relates to purification of proteins using hydrophobic interaction chromatography.

BACKGROUND OF THE INVENTION

Hydrophobic interaction chromatography (HIC) is a method for separating proteins based on the strength of their relative hydrophobic interactions with a hydrophobic adsorbent. Hydrophobicity is generally defined as the repulsion between a non-polar compound and a polar environment, such as water. Hydrophobic "interactions" are essentially the tendency of a polar environment to exclude non-polar (i.e., hydrophobic) compounds from the polar environment and force aggregation of the hydrophobic amongst themselves. The phenomenon of hydrophobic interactions is applied to the separation of proteins by using an aqueous salt solution to force a hydrophobic protein in a sample to aggregate with or bind adsorptively to hydrophobic functional groups (the adsorbent) affixed to a solid support. The adsorbed proteins are released from the adsorbent by eluting with decreasing salt concentrations which reverse the environment promoting the hydrophobic interactions, leading to loss of hydrophobic interactions between the proteins and the support and release of the protein from the support in order of increasing hydrophobicity (with the least hydrophobic proteins being released first).

Recombinant proteins typically contain a variety of impurities that need to be removed before the product is pharmaceutically acceptable. Some of these impurities may include host cell proteins (HCPs) from the host cell system in which they are expressed. For a CHO system, these impurities are referred to as CHO Host Cell Proteins (CHOP). In addition to these impurities, the protein as expressed during cell culture may also contain variant forms of the product protein, for example, a misfolded form of the target protein. Other impurities may be added to the product stream or generated as a result of the purification process, such as higher molecular weight aggregates of the protein or leached Protein A. These impurities have a wide range of retentions on different modes of chromatography and removal of such a broad spectrum of impurities is difficult, typically requiring multiple steps involving different modes of chromatography.

HIC may be utilized to separate proteins using two different approaches. In the first HIC approach, referred to as the "bind and elute" mode, the mixture containing the target protein is contacted with the hydrophobic adsorbent under conditions where the target protein binds to the adsorbent, while contaminants (or as much of the contaminants as possible) do not bind and flow through. In the "bind and elute" mode, the target protein may be recovered by applying to the adsorbent/protein complex a salt concentration applied in a gradual or step-wise reduced gradient, to selectively release the various bound proteins and contaminants and collecting discreet fractions until the fraction containing the more purified protein is obtained. In a process where a target protein is bound to the column (while allowing contaminants to flow through), adsorbents having greater hydrophobicity are typically used to bind a broader range of proteins which will be collected in a specific fraction release at a specific salt concentration in the course of applying the salt gradient. In the second HIC approach, referred to as the "flow-through" mode, the mixture containing the target protein is contacted with the hydrophobic adsorbent under conditions where the contaminants (or as much of the contaminants as possible) bind to the adsorbent, while the target protein (and as few contaminants as possible) does not bind and flows through. In this mode, the use of less hydrophobic adsorbents, such as those having lower molecular weight alkyl groups, are preferred, since a lower binding capacity is needed for conditions under which the target protein does not bind. As one would expect, however, use of HIC in the flow-through mode has been of limited usefulness because the conditions needed to allow the target protein to flow through inherently result in lower binding capacities, leading to early elimination of the target protein, or elimination of the target protein along with contaminants.

While several different modalities of chromatography can be employed to remove a particular class of impurities, very few chromatographic steps are capable of removing all these impurities from a product. Thus, there is need for a purification process that can be employed generically for removal of these impurities from a recombinant protein.

SUMMARY OF THE INVENTION

In accordance with the present invention, it has been discovered that hydrophobic interaction chromatography using a hydrophobic adsorbent comprising branched hydrocarbon functional groups, such as branched alkyl groups, is highly selective in binding protein contaminants, while not binding the target protein, thus allowing the target protein to be recovered in the flow-through fraction. Use of HIC in flow-through has been found to be surprisingly efficient, resulting in a significantly higher recovery of the target protein in a single step, thus simplifying and improving the efficiency and cost of the protein purification process.

The present invention includes a process for separating a target protein (such as a recombinant protein produced in a cell culture) from a mixture containing the target protein and contaminants which comprises: contacting the mixture with a hydrophobic adsorbent comprising branched hydrocarbon functional groups in an aqueous salt solution, and collecting the portion of the mixture that does not bind to the hydrophobic adsorbent, which contains the target protein.

In another embodiment, the present invention includes a process for separating a recombinant protein, produced as a product of cell culture expression in a host cell, from a mixture containing the protein and cell culture contaminants, which comprises: contacting the mixture with a hydrophobic adsorbent comprising branched hydrocarbon functional groups in an aqueous salt solution, and collecting the portion of the mixture that does not bind to the hydrophobic adsorbent, which contains the target protein.

In another embodiment, the present invention includes a process for separating a recombinant Fc fusion protein, produced as a product of cell culture expression in a host cell, from a mixture containing the protein and cell culture contaminants, which comprises: contacting the mixture with a hydrophobic adsorbent comprising branched hydrocarbon functional groups in an aqueous salt solution, and collecting the portion of the mixture that does not bind to the hydrophobic adsorbent, which contains the target protein.

In yet another embodiment, the present invention includes a process for separating a recombinant target protein, produced as a product of cell culture expression in a host cell, from a mixture containing the protein and contaminants, which comprises: preparing a chromatography column having a support comprising hydrophobic branched alkyl functional groups, wherein the branched alkyl functional groups have from 4 to 8 carbon atoms, at least one of which is a tertiary carbon atom, preparing the mixture in an aqueous solution having a salt concentration such that the contaminants bind to the column while the target protein in the mixture does not bind to the column; contacting the mixture with the column; and collecting from the column the portion of the mixture that does not bind to the column, which contains the recombinant target protein.

A process for removing a misfolded variant of a recombinant target protein from a mixture containing correctly folded variants and misfolded variants of the target protein, which comprises contacting the mixture with a hydrophobic adsorbent comprising branched hydrocarbon functional groups in an aqueous salt solution; and collecting the portion of the mixture that does not bind to the hydrophobic adsorbent, which contains the correctly folded variant of the target protein.

A process for removing Protein A from a mixture containing a target protein and Protein A, which comprises: contacting the mixture with a hydrophobic adsorbent comprising branched hydrocarbon functional groups in an aqueous salt solution; and collecting the portion of the mixture that does not bind to the hydrophobic adsorbent, which contains the target protein.

In other embodiments of the present invention, the hydrophobic adsorbent comprises a branched alkyl functional group. In another embodiment, the branched alkyl functional group has from 3 to 8 carbon atoms, and more preferably from 4 to 6 carbon atoms. In another embodiment, the branched alkyl functional group contains a sec-carbon, a tert-carbon or a neo-carbon atom. In another embodiment, the branched alkyl functional group may be selected from one or more of the group consisting of sec-butyl, tert-butyl, tert-pentyl, and neopentyl. In another embodiment, the branched alkyl functional group is tert-butyl.

BRIEF DESCRIPTION OF THE FIGURES

FIG. 2 is an SDS-PAGE gel showing the load and flow-through fractions from FIG. 1. Lane 1 shows molecular weight standards, lane 2 shows the HIC load, and lane 3 shows the HIC flow-through.

FIGS. 4a, 4b, 4c and 4d are a series of graphs that compare the HIC load to the HIC flowthrough pool by various analytical methods including size exclusion chromatography (SEC) (FIG. 4a), leached Protein A ELISA (FIG. 4b), HIC (FIG. 4c) and fCHOP ELISA (FIG. 4d).

DETAILED DESCRIPTION OF THE INVENTION

Definitions

Figure 1:
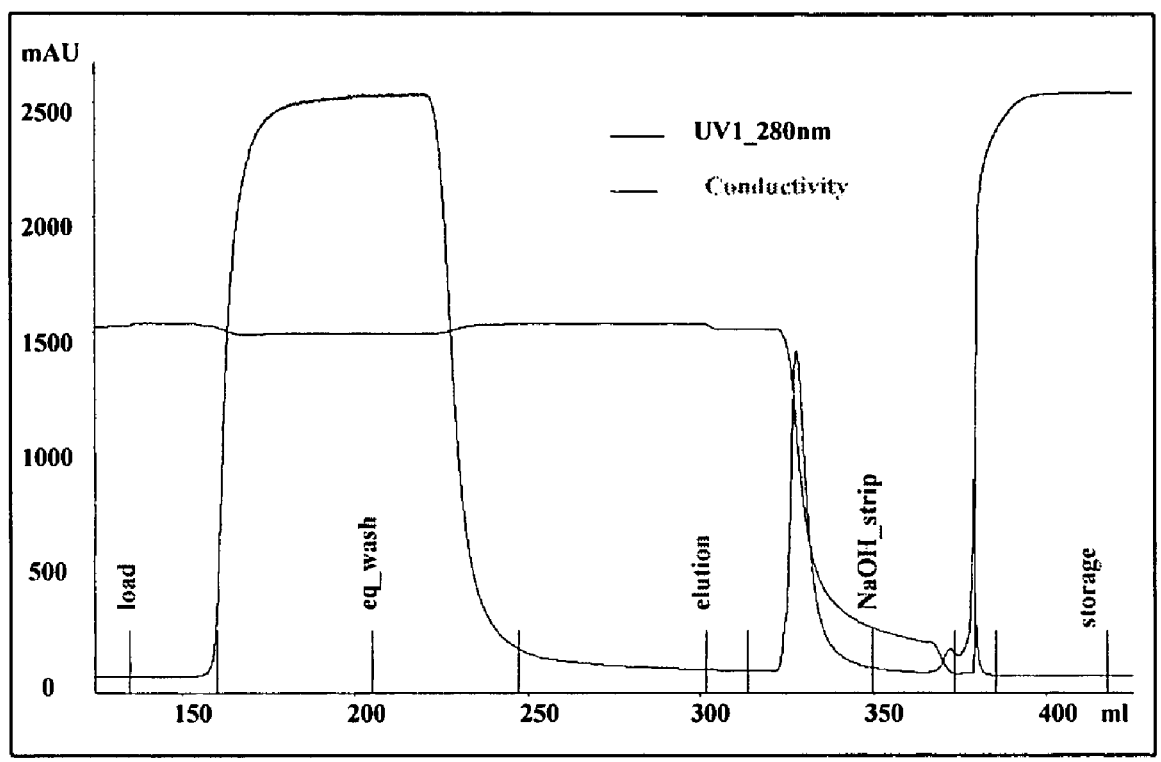
FIG. 1 is a chromatogram showing the purification of IL1R-II in the flow-through step on a Macroprep t-butyl HIC resin.

Adsorbent: An adsorbent is at least one molecule affixed to a solid support, or at least one molecule that is, itself, a solid, which is used to perform chromatography, such as hydrophobic interaction chromatography. In the context of hydrophobic interaction chromatography, the adsorbent is a hydrophobic functional group.

Hydrophobic interaction chromatography or HIC: Hydrophobic interaction chromatography (HIC) is chromatography that utilizes specific reversible hydrophobic interactions between biomolecules in an aqueous salt solution as a basis for protein separation. In practice, HIC involves using an adsorbent, such as a hydrophobic aliphatic or aromatic hydrocarbon functional group affixed to a solid support, to chromatographically separate molecules that bind to the adsorbent from those proteins that do not.

Antibody: An antibody is a protein or complex of proteins, each of which comprises at least one variable antibody immunoglobulin domain and at least one constant antibody immunoglobulin domain. Antibodies may be single chain antibodies, dimeric antibodies, or some higher order complex of proteins including, but not limited to, heterodimeric antibodies.

Chromatography: Chromatography is the separation of chemically different molecules in a mixture from one another by contacting the mixture with an adsorbent, wherein one class of molecules reversibly binds to or is adsorbed onto the adsorbent. Molecules that are least strongly adsorbed to or retained by the adsorbent are released from the adsorbent under conditions where those more strongly adsorbed or retained are not.

Constant antibody immunoglobulin domain: A constant antibody immunoglobulin domain is an immunoglobulin domain that is identical to or substantially similar to a $C_L$, $C_H1$, $C_H2$, $C_H3$, or $C_H4$, domain of human or animal origin. See e.g. Charles A Hasemann and J. Donald Capra, Immunoglobulins: Structure and Function, in William E. Paul, ed., *Fundamental Immunology*, Second Edition, 209, 210-218 (1989), which is incorporated by reference herein in its entirety.

Contaminant: A contaminant is any foreign or objectionable molecule, particularly a biological macromolecule such as a DNA, an RNA, or a protein, other than the protein being purified that is present in a sample of a protein being purified. Contaminants include, for example, other host cell proteins from cells used to recombinantly express the protein being purified, proteins that are part of an absorbent used in an affinity chromatography step that may leach into a sample during prior affinity chromatography step, such as Protein A, and misfolded variants of the target protein itself.

$F_C$: $F_C$ refers to the $F_C$ portion of an antibody, and includes human or animal immunoglobulin domains $C_H2$ and $C_H3$ or immunoglobulin domains substantially similar to these. For purposes of the invention, the biological activity of an $F_C$ portion of an antibody for the purpose of determining substantial similarity is the ability to be bound by a second protein that binds to naturally-occurring $F_C$ portions of antibodies, such as Protein A or Protein G. For discussion, see Hasemann and Capra, supra, at 212-213.

Host cell proteins: Host cell proteins are proteins encoded by the naturally-occurring genome of a host cell into which DNA encoding a protein that is to be purified is introduced. Host cell proteins may be contaminants of the protein to be purified, the levels of which may be reduced by purification. Host cell proteins can be assayed for by any appropriate method including gel electrophoresis and staining and/or ELISA assay, among others. Host cell proteins include, for example, Chinese Hamster Ovary (CHO) proteins (CHOP) produced as a product of expression of recombinant proteins.

IL1RII: IL1R-II refers to the Type II (B Cell) Interleukin-1 receptor described in U.S. Pat. Nos. 6,521,740; 5,464,937; and 5,350,683, each of which is incorporated by reference herein in its entirety.

Polypeptide: For the purposes of the invention, "polypeptide" is used interchangeably with "protein."

Protein: A protein is any chain of at least five amino acids linked by peptide bonds.

Protein A: Protein A is a protein originally discovered in the cell wall of *Stapphylococcus* that binds specifically to an $F_C$ portion of IgG antibody. For purposes of the invention, "Protein A" is any protein identical or substantially similar to Stapphylococcal Protein A, including commercially available and/or recombinant forms of Protein A. For purposes of the invention, the biological activity of Protein A for the purpose of determining substantial similarity is the capacity to bind to an $F_C$ portion of IgG antibody.

Purify: To purify a protein means to reduce the amounts of foreign or objectionable elements, especially biological macromolecules such as proteins or DNA, that may be present in a sample of the protein. The presence of foreign proteins may be assayed by any appropriate method including gel electrophoresis and staining and/or ELISA assay. The presence of DNA may be assayed by any appropriate method including gel electrophoresis and staining and/or assays employing polymerase chain reaction.

Recombinant fusion protein: A recombinant fusion protein is any protein that comprises part or all of two or more proteins that are not fused in their natural state. Examples of such proteins include, but are not limited to, human receptor activator of NF-KappaB fused to an $F_C$ portion of an antibody (huRANK:$F_C$), tunica internal endothelial cell kinase-delta fused to an $F_C$ portion of an antibody (TEKdelta:$F_C$), and tumor necrosis factor receptor fused to an $F_C$ portion of an antibody (TNFR:$F_C$).

RANK: "RANK" refers to a receptor activator of NF kappa β proteins comprising amino acid sequences that are identical or substantially similar to the sequence of a native RANK. Biological activity for the purpose of determining substantial similarity means the capacity to bind Rank ligand (RANK-L), to transduce a biological signal initiated by RANK-L binding to a cell, or to cross-react with anti-RANK antibodies raised against RANK from natural (i.e., non-recombinant) sources. A RANK protein may be any mammalian RANK, including murine or human RANK proteins. Such RANK proteins are described in U.S. Pat. Nos. 6,017,729; 6,562,948; and 6,271,349, each of which is incorporated by reference herein in its entirety.

RANK:$F_C$: RANK:$F_C$ is a recombinant fusion protein comprising all or part of an extracellular domain of a RANK fused to an $F_C$ region of an antibody, as described in U.S. Pat. Nos. 6,017,729; 6,562,948; and 6,271,349, each of which is incorporated by reference herein in its entirety.

Separate or Remove: A protein is separated (or removed) from a mixture comprising the protein and other contaminants when the mixture is subjected to a process such that the concentration of the target protein is higher in the resulting product than the starting product.

TNFR: "TNFR" refers to proteins comprising amino acid sequences that are identical or substantially similar to the sequence of a native mammalian tumor necrosis factor receptor (TNFR). Biological activity for the purpose of determining substantial similarity means the capacity to bind tumor necrosis factor (TNF), to transduce a biological signal initiated by TNF binding to a cell, or to cross-react with anti-TNFR antibodies raised against TNFR from natural (i.e., non-recombinant) sources. A TNFR may be any mammalian TNFR, including murine or human TNFRs. Such TNFRs are described in U.S. Pat. No. 5,395,760, which is incorporated by reference herein in its entirety, and in U.S. Pat. No. 5,610,279, which is incorporated by reference herein in its entirety. A particularly preferred TNFR is that described in U.S. Pat. No. 5,395,760, which has an apparent molecular weight by SDS-PAGE of about 80 kilodaltons in its glycosylated form.

TNFR:$F_C$: TNFR: $F_C$ is a recombinant fusion protein comprising all or part of an extracellular domain of a TNFR fused to an $F_C$ region of an antibody. Such an extracellular domain includes, but is not limited to, amino acid sequences substantially similar to amino acids 1-163, 1-185, or 1-235 of FIG. 2A of U.S. Pat. No. 5,395,760.

Variable antibody immunoglobulin domain: A variable antibody immunoglobulin domain is an immunoglobulin domain that is identical or substantially similar to a $V_L$ or a $V_H$ domain of human or animal origin. For purposes of the invention, the biological activity of a variable antibody immunoglobulin domain for the purpose of determining substantial similarity is antigen binding.

Description of the Process

The process of purifying a protein often requires numerous steps, with each step resulting in a further reduction in yield. Hydrophobic interaction chromatography is one of many techniques commonly used. Protein purification by HIC may be performed in a column containing a hydrophobic media (typically a column packed with modified support of methacrylate copolymer or agarose beads to which is affixed an adsorbent consisting of mildly hydrophobic functional groups, such as small alkyl or aryl hydrocarbon groups). The column is equilibrated with a buffer at high salt concentration and a sample containing a mixture of proteins (the target protein, plus contaminating proteins) in a compatible non-denaturing high salt solution, is loaded onto the column. As the mixture passes through the column, the target protein binds to the adsorbent within the column, while unbound contaminants flow through. Bound protein is then eluted from the column with a reduced salt concentration. Typically, the target protein may be recovered by eluting the column with a salt concentration applied in a gradual or step-wise reduced gradient, to selectively release the various bound proteins at the particular salt concentration conducive to their release, and collecting discreet fractions until the fraction containing the more purified protein is obtained. By collecting flow-through fractions over discreet periods of time, fractions containing specific proteins can be isolated. In a process where a target protein is bound to the column (while allowing contaminants to flow through), adsorbents having greater hydrophobicity are typically used to bind a broader range of proteins which will be collected in a specific fraction conducive to the release of the protein. Less hydrophobic adsorbents, such as those having lower molecular weight alkyl groups, have been of limited efficacy because the resin generally demonstrates lower binding capacities leading to early elimination in HIC resin screens.

The present invention relates to a process for separating the target protein from a mixture comprising the target protein and contaminants using hydrophobic interaction chromatography (HIC). In contrast to the bind and elute approach described above, however, the present invention applies HIC in a flow-through mode to separate the target protein by binding the contaminating proteins (rather than the target protein) to the chromatography support, and collecting the purified target protein in the unbound flow-through fraction. Thus, the present invention contemplates that HIC conditions will be such that contaminating proteins bind to the chromatography support, while the target protein does not bind. Separation of the target protein in the flow-through fraction greatly simplifies the separation process. In flow-through mode, HIC may be operated under higher loading capacities since only the impurities bind on the resin and the product flows through. Furthermore, HIC flow through mode enables use of lower salt concentrations since low to moderately hydrophobic proteins of interest elute preferentially at such lower salt concentrations.

The process of the invention can, of course, be used in combination with other protein purification methodologies, such as salt precipitation, affinity chromatography, hydroxyapatite chromatography, reverse phase liquid chromatography, ion-exchange chromatography, or any other commonly used protein purification technique. It is contemplated, however, that the process of the present invention will eliminate or significantly reduce the need for other purification steps.

Any or all chromatographic steps of the present invention can be carried out by any mechanical means. Chromatography may be carried out, for example, in a column. The column may be run with or without pressure and from top to bottom or bottom to top. The direction of the flow of fluid in the column may be reversed during the chromatography process. Chromatography may also be carried out using a batch process in which the solid media is separated from the liquid used to load, wash, and elute the sample by any suitable means, including gravity, centrifugation, or filtration. Chromatography may also be carried out by contacting the sample with a filter that absorbs or retains some molecules in the sample more strongly than others. In the following description, the various embodiments of the present invention are described in the context of chromatography carried out in a column. It is understood, however, that use of a column is merely one of several chromatographic modalities that may be used, and the illustration of the present invention using a column does not limit the application of the present invention to column chromatography, as those skilled in the art may readily apply the teachings to other modalities as well, such as those using a batch process or filter.

The present in invention relates to a process for separating proteins on the basis of their ability to selectively bind to a hydrophobic chromatography medium. The hydrophobic chromatography medium is comprised of a solid support to which is affixed a hydrophobic adsorbent comprising a branched hydrocarbon functional group. A sample containing the target protein to be purified is contacted with the hydrophobic adsorbent under conditions that cause contaminants to selectively bind to the adsorbent, while the target protein does not bind. The portion of the mixture that does not bind (and which contains the target protein) is then separated from the adsorbent under conditions that do not interfere with the binding of the contaminants to the adsorbent.

The hydrophobic chromatography medium may be represented by the formula S—X—R, where S is the support, multiple —X—R groups are covalently attached to the support, R is any one or more branched hydrocarbon functional group, and X is a hetero atom or group of atoms that serve to covalently bond R to the support. The support used in the present invention comprises a resin matrix prepared by any suitable means widely known to those skilled in the art. In general, the support may be of any material that is compatible with protein separations, is water insoluble, and can be modified by covalent linkage to form the —X—R linkage with the R functional group. Suitable supports may be any currently available or later developed materials having the characteristics necessary to practice the claimed method, and may be based on any synthetic, organic, or natural polymers. For example, commonly used support substances include organic materials such as cellulose, polystyrene, agarose, sepharose, polyacrylamide polymethacrylate, dextran and starch, and inorganic materials, such as charcoal, silica (glass beads or sand) and ceramic materials. Suitable solid supports are disclosed, for example, in Zaborsky "Immobilized Enzymes" CRC Press, 1973, Table IV on pages 28-46.

Specific HIC support materials that may be used include methacrylate polymer and activated agarose (see, Porath, Nature 215, 1491 (1967) and Cuatrecasas, J. Biol. Chem. 245, 3059, (1970)). In certain instances it may be necessary to activate the support so that it will react with a functional R group to produce the —X—R moiety. Therefore, it is to be understood that if the source material for the support, for example agarose, is not itself amenable to reaction with a particular functional group, it may be conditioned or activated so that it will be amenable to such reactions. An example is the activation of agarose by treatment with cyanogen halide as described, for example, by Porath et al. in Nature, 215, 1491 (1967) and by Cuatrecsas in J. Biol. Chem. 245, 3059 (1970). The HIC support material may also be methacrylate copolymer bead resins (such as Macro-Prep t-butyl HIC support resins, supplied by Bio-Rad Laboratories, Inc.) to which branched hydrocarbon groups have been covalently attached. Appropriate characteristics include average bead sizes of 30 to 100 microns, functional group densities of 5 to 50 micromoles per ml gel, and beads containing 4-6% agarose. Other types of support materials include polystyrene/divinyl benzene matrix particles, which can be coupled to appropriate functional R groups described below. The selection and use of such support materials is well-known to those skilled in the art.

As used in the present invention, R may be aromatic, aliphatic or mixed aromatic/aliphatic groups having sufficiently moderate to low hydrophobicity that they selectively bind protein contaminants while not binding a target protein. In one embodiment of the present invention, R is of low to moderate hydrophobicity. In another embodiment, the branched hydrocarbon R group is a branched alkyl group. The branched alkyl functional groups may have in various embodiments, respectively, from 3 to about 8 carbon atoms, from 4 to 7, from 4 to 6, from 4 to 5, or 4 carbon atoms. By way of example, the branched alkyl functional R group may be selected from one or more of the group consisting of isopropyl, isobutyl, sec-butyl, and tert-butyl isopentyl, sec-pentyl, tert-pentyl, neopentyl, isohexyl, sec-hexyl, tert-hexyl, and other higher branched alkyl groups having up to about 8 carbon atoms. In other embodiments, these branched alkyl groups may be those having tert-carbon (carbon bonded to three other carbons) or neo-carbon (carbon bonded to four other carbon) moieties, such as tert-butyl, tert-pentyl, and neopentyl. In another embodiment, R has a tert-carbon atom, such as tert-butyl, tert-pentyl and tert-hexyl. In another embodiment, R is tert-butyl. As indicated in the examples below, as between two R groups having the same number of carbon atoms, the most effective functional groups are those that are more highly branched. For example, tert-butyl, (having 4 carbon atoms, one of which is a tertiary carbon) is surprisingly more effective than linear-butyl (also having 4 carbon atoms, but which is unbranched).

X may be any hetero atom, such as O or S, or group of atoms, such as NH, which may also carry an electric charge in the form of an ion. A variety of commercially available hydrophobic interaction chromatography resins can be used, and the present invention is not limited to any particular resin.

One example of an HIC column having a branched alkyl functional group is Macroprep t-butyl (BioRad Laboratories, Inc).

Prior to equilibration and chromatography, the HIC chromatography media (the support and adsorbent affixed to the support) may be pre-equilibrated in a chosen solution, e.g. a salt and/or buffer solution. Pre-equilibration serves the function of displacing a solution used for regenerating and/or storing the chromatography medium. One of skill in the art will realize that the composition of the pre-equilibration solution depends on the composition of the storage solution and the solution to be used for the subsequent chromatography. Thus, appropriate pre-equilibration solutions may include the same buffer or salt used for performing the chromatography, optionally, at a higher concentration than is used to perform chromatography. Buffers and salts that can be used for chromatography are discussed below. For example, when the solution used to perform chromatography comprises sodium phosphate at a given concentration, pre-equilibration may take place in a in a solution comprising sodium phosphate at a higher concentration. As an illustration of this, if the solution used to perform chromatography comprises sodium phosphate at between about 0.5 millimolar and about 50 millimolar, pre-equilibration may occur in a solution comprising sodium phosphate at concentrations between about 0.2 molar and about 0.5 molar, more preferably in concentrations of sodium phosphate between about 0.3 molar and about 0.4 molar, inclusive.

Before the sample is applied to the column, the column can be equilibrated in the buffer or salt that will be used to chromatograph the protein. As discussed below, chromatography (and loading of the protein to be purified) can occur in a variety of buffers or salts including sodium, potassium, ammonium, magnesium, calcium, chloride, fluoride, acetate, phosphate, and/or citrate salts and/or Tris buffer. Citrate buffers and salts are preferred by those skilled in the art for their ease of disposal. Such buffers or salts can have a pH of at least about 5.5. In some embodiments, equilibration may take place in a solution comprising a Tris or a sodium phosphate buffer. Optionally, the sodium phosphate buffer is at a concentration between about 0.5 millimolar and about 50 millimolar, more preferably at a concentration between about 15 millimolar and 35 millimolar. Preferably, equilibration takes place at a pH of at least about 5.5. Equilibration may take place at pHs between about 6.0 and about 8.6, preferably at pHs between about 6.5 and 7.5. Most preferably, the solution comprises a sodium phosphate buffer at a concentration of about 25 millimolar and at a pH of about 6.8.

The target protein that is to be purified can be produced by living host cells that have been genetically engineered to produce the protein. Methods of genetically engineering cells to produce proteins are well known in the art. See e.g. Ausabel et al., eds. (1990), Current Protocols in Molecular Biology (Wiley, New York). Such methods include introducing nucleic acids that encode and allow expression of the protein into living host cells. These host cells can be bacterial cells, fungal cells, or, preferably, animal cells grown in culture. Bacterial host cells include, but are not limited to, *Escherichia coli* cells. Examples of suitable *E. coli* strains include: HB101, DH5α, GM2929, JM109, KW251, NM538, NM539, and any *E. coli* strain that fails to cleave foreign DNA. Fungal host cells that can be used include, but are not limited to, *Saccharomyces cerevisiae, Pichia pastoris* and *Aspergillus* cells. A few examples of animal cell lines that can be used are CHO, VERO, BHK, HeLa, Cos, MDCK, 293, 3T3, and WI38. New animal cell lines can be established using methods well know by those skilled in the art (e.g., by transformation, viral infection, and/or selection). Optionally, the protein can be secreted by the host cells into the medium.

Protein concentration of a sample at any stage of purification can be determined by any suitable method. Such methods are well known in the art and include: 1) colorimetric methods such as the Lowry assay, the Bradford assay, the Smith assay, and the colloidal gold assay; 2) methods utilizing the UV absorption properties of proteins; and 3) visual estimation based on stained protein bands on gels relying on comparison with protein standards of known quantity on the same gel. See e.g. Stoschek (1990), Quantitation of Protein, in *Guide to Protein Purification*, Methods in Enzymol. 182: 50-68.

The protein purification process of the present invention is applicable to any protein. The process is particularly useful in purifying proteins that are less hydrophobic than the contaminants from which they are being separated. The process is particularly useful, for example, in purifying proteins of low to moderate hydrophobicity, such as recombinantly produced proteins, or proteins comprising an $F_C$ region of an antibody, both of which tend to have relatively low to moderate hydrophobicities. Proteins comprising one or more constant antibody immunoglobulin domain(s) may, but need not, comprise a single or multiple variable antibody immunoglobulin domain(s). $F_c$ fusion proteins may be a naturally-occurring protein or a recombinant fusion protein. It may comprise an $F_c$ portion of an antibody. It may also comprise a non-antibody protein.

Some proteins specifically contemplated for use with the invention include recombinant fusion proteins comprising one or more constant antibody immunoglobulin domains, optionally an $F_C$ portion of an antibody, and a protein identical to or substantially similar to one of the following proteins: a flt3 ligand (as described in international application no. WO 94/28391, which is incorporated by reference herein in its entirety), a CD40 ligand (as described in U.S. Pat. No. 6,087,329, which is incorporated by reference herein in its entirety), erythropoeitin, thrombopoeitin, calcitonin, Fas ligand, ligand for receptor activator of NF-kappa B (RANKL), tumor necrosis factor (TNF)-related apoptosis-inducing ligand (TRAIL, as described in international application no. WO 97/01633, which is incorporated by reference herein in its entirety), thymic stroma-derived lymphopoietin, granulocyte colony stimulating factor, granulocyte-macrophage colony stimulating factor (GM-CSF, as described in Australian Patent No. 588819, which is incorporated by reference herein in its entirety), mast cell growth factor, stem cell growth factor, epidermal growth factor, RANTES, growth hormone, insulin, insulinotropin, insulin-like growth factors, parathyroid hormone, interferons, nerve growth factors, glucagon, interleukins 1 through 18, colony stimulating factors, lymphotoxin-β, tumor necrosis factor (TNF), leukemia inhibitory factor, oncostatin-M, and various ligands for cell surface molecules ELK and Hek (such as the ligands for eph-related kinases or LERKS). Descriptions of proteins that can be purified according to the inventive methods may be found in, for example, *Human Cytokines: Handbook for Basic and Clinical Research, Vol. II* (Aggarwal and Gutterman, eds. Blackwell Sciences, Cambridge, Mass., 1998); *Growth Factors: A Practical Approach* (McKay and Leigh, eds., Oxford University Press Inc., New York, 1993); and *The Cytokine Handbook* (A. W. Thompson, ed., Academic Press, San Diego, Calif., 1991).

Proteins contemplated by the invention also include recombinant fusion proteins comprising one or more constant antibody immunoglobulin domains, optionally an $F_C$ portion of an antibody, plus a receptor for any of the above-mentioned proteins or proteins substantially similar to such receptors. These receptors include: both forms of TNFR (referred to as p55 and p75), Interleukin-1 receptors types I and II (as described in EP Patent No. 0 460 846, U.S. Pat. No. 4,968,607, and U.S. Pat. No. 5,767,064, which are incorporated by reference herein in their entirety), Interleukin-2 receptor, Interleukin-4 receptor (as described in EP Patent No. 0 367 566 and U.S. Pat. No. 5,856,296, which are incorporated by reference herein in their entirety), Interleukin-15 receptor, Interleukin-17 receptor, Interleukin-18 receptor, granulocyte-macrophage colony stimulating factor receptor, granulocyte colony stimulating factor receptor, receptors for oncostatin-M and leukemia inhibitory factor, receptor activator of NF-kappa B (RANK, as described in U.S. Pat. No. 6,271,349, which is incorporated by reference herein in its entirety), receptors for TRAIL (including TRAIL receptors 1, 2, 3, and 4), and receptors that comprise death domains, such as Fas or Apoptosis-Inducing Receptor (AIR).

Other proteins that may be purified using the process of the invention include differentiation antigens (referred to as CD proteins) or their ligands or proteins substantially similar to either of these, which are fused to at least one constant antibody immunoglobulin domain, optionally an $F_C$ portion of an antibody. Such antigens are disclosed in *Leukocyte Typing VI* (*Proceedings of the VIth International Workshop and Conference*, Kishimoto, Kikutani et al., eds., Kobe, Japan, 1996). Similar CD proteins include CD27, CD30, CD39, CD40, and ligands thereto (CD27 ligand, CD30 ligand, etc.). Several of the CD antigens are members of the TNF receptor family, which also includes 41BB ligand and OX40. The ligands are often members of the TNF family, as are 41BB ligand and OX40 ligand. Accordingly, members of the TNF and TNFR families can also be purified using the present invention.

Enzymatically active proteins or their ligands can also be purified according to the invention. Examples include recombinant fusion proteins comprising at least one constant antibody immunoglobulin domain plus all or part of one of the following proteins or their ligands or a protein substantially similar to one of these: metalloproteinase-disintegrin family members, various kinases, glucocerebrosidase, superoxide dismutase, tissue plasminogen activator, Factor VIII, Factor IX, apolipoprotein E, apolipoprotein A-I, globins, an IL-2 antagonist, alpha-1 antitrypsin, TNF-alpha Converting Enzyme, ligands for any of the above-mentioned enzymes, and numerous other enzymes and their ligands.

The method of the invention may also be used to purify antibodies or portions thereof and chimeric antibodies, i.e. antibodies having human constant antibody immunoglobulin domains coupled to one or more murine variable antibody immunoglobulin domain, or fragments thereof. The method of the invention may also be used to purify conjugates comprising an antibody and a cytotoxic or luminescent substance. Such substances include: maytansine derivatives (such as DM1); enterotoxins (such as a Staphlyococcal enterotoxin); iodine isotopes (such as iodine-125); technium isotopes (such as Tc-99m); cyanine fluorochromes (such as Cy5.5.18); and ribosome-inactivating proteins (such as bouganin, gelonin, or saporin-S6). Examples of antibodies or antibody/cytotoxin or antibody/luminophore conjugates contemplated by the invention include those that recognize any one or combination of the above-described proteins and/or the following antigens: CD2, CD3, CD4, CD8, CD11a, CD14, CD18, CD20, CD22, CD23, CD25, CD33, CD40, CD44, CD52, CD80 (B7.1), CD86 (B7.2), CD147, IL-1α, IL-1β, IL-4, IL-5, IL-8, IL-10, IL-2 receptor, IL-4 receptor, IL-6 receptor, IL-13 receptor, IL-18 receptor subunits, PDGF-β, VEGF, TGF, TGF-β2, TGF-β1, EGF receptor, VEGF receptor, C5 complement, IgE, tumor antigen CA125, tumor antigen MUC1, PEM antigen, LCG (which is a gene product that is expressed in association with lung cancer), HER-2, a tumor-associated glycoprotein TAG-72, the SK-1 antigen, tumor-associated epitopes that are present in elevated levels in the sera of patients with colon and/or pancreatic cancer, cancer-associated epitopes or proteins expressed on breast, colon, squamous cell, prostate, pancreatic, lung, and/or kidney cancer cells and/or on melanoma, glioma, or neuroblastoma cells, the necrotic core of a tumor, integrin alpha 4 beta 7, the integrin VLA-4, B2 integrins, TRAIL receptors 1, 2, 3, and 4, RANK, RANK ligand, TNF-α, the adhesion molecule VAP-1, epithelial cell adhesion molecule (EpCAM), intercellular adhesion molecule-3 (ICAM-3), leukointegrin adhesin, the platelet glycoprotein gp IIb/IIIa, cardiac myosin heavy chain, parathyroid hormone, rNAPc2 (which is an inhibitor of factor VIIa-tissue factor), MHC I, carcinoembryonic antigen (CEA), alpha-fetoprotein (AFP), tumor necrosis factor (TNF), CTLA-4 (which is a cytotoxic T lymphocyte-associated antigen), Fc-γ-1 receptor, HLA-DR 10 beta, HLA-DR antigen, L-selectin, IFN-γ, Respiratory Syncitial Virus, human immunodeficiency virus (HIV), hepatitis B virus (HBV), *Streptococcus mutans*, and *Staphlycoccus aureus*.

The invention may also be used to purify anti-idiotypic antibodies, or substantially similar proteins, including but not limited to anti-idiotypic antibodies against: an antibody targeted to the tumor antigen gp72; an antibody against the ganglioside GD3; or an antibody against the ganglioside GD2.

In the protein purification process of the present invention, the sample containing the target protein and contaminants may be loaded onto the adsorbent support under conditions in which the cell culture contaminants to bind to the stationary phase column, while permitting the protein of choice to pass through in the flow-through fraction. HIC is typically performed by loading the protein sample onto the chromatography column in an aqueous solution comprising a buffer and/or a salt. Lowering the ionic strength of the solution (i.e., decreasing the concentration of salt) reduces the tendency of hydrophobic materials to be retained by the column. Suitable buffers include, but are not limited to phosphate buffers, Tris buffers, acetate buffers, and/or citrate buffers. Acceptable salts may include, but are not limited to sodium chloride, ammonium chloride, potassium chloride, sodium acetate, ammonium acetate, sodium sulfate, ammonium sulfate, ammonium thiocyanate, sodium citrate, sodium phosphate, and potassium, magnesium, and calcium salts thereof, and combinations of these salts. In other embodiments, the salts include sodium citrate and sodium chloride. Acceptable ranges of salt concentrations used for HIC systems are typically in the range of from 0 to about 2M sodium citrate, 0 to about 4M sodium chloride, 0 to about 3M ammonium sulfate, 0 to about 1M sodium sulfate and 0 to about 2M sodium phosphate. The ranges of salt concentration may include 0 to about 1M sodium citrate, 0 to about 2M sodium chloride, 0 to about 1.5M ammonium sulfate, 0 to about 1M sodium sulfate and 0 to about 1.5M sodium phosphate. Other buffers and salts can also be used. After loading, the adsorbent can be washed with more of the same solution to cause the target protein (unbound to the adsorbent) to flow through the adsorbent. The protein is then collected in the flow-through fraction. Conditions for binding contaminants, while the target protein does not bind, can be easily optimized by those skilled in the art. The salt concentrations discussed herein are exemplary, and other salts and salt concentrations can be used by varying flow rates, temperatures, and elution times as is known in the art.

Conditions under which these columns are used vary with the specific columns as is known in the art. For most proteins of interest, the pH range may be between about 6.0 and about 8.6, or alternatively between about 6.5 and about 7.5. However, certain proteins are known to be resistant to pH extremes, and a broader range may be possible. Typical conditions include a pH range of 5-7 and a sodium citrate concentration range of 0 to about 0.8M (e.g. 0.5M sodium citrate, pH 6.0).

One skilled in the art will be guided by the knowledge in the art in determining which buffer or salt is appropriate for the particular protein being purified. Moreover, a skilled artisan can easily determine the optimal concentration of the selected buffer or salt to use by, for example, establishing particular buffer or salt conditions under which contaminants bind to an HIC column while the protein of interest flows through in the flow-through fraction. Fractions of the effluent of the column can be collected and analyzed to determine the concentration of buffer or salt at which the target protein and the contaminants elute. Suitable analyses include, for example, a measurement of electrical conductance with a conductivity meter (to determine the salt concentration in the sample) plus gel electrophoresis or ELISA assay (to determine the identity of the proteins in the sample). Optionally, the column can be washed with more of the same solution in which the protein sample was loaded, and this wash solution can also be collected and combined with the flow-through liquid.

Subsequent to collection of the flow through and, optionally, the wash, which comprises the protein being purified, proteins that may remain bound to the column may be released by stripping the chromatography medium using a solution comprising the buffer or salt used for chromatography, but at a lower ionic strength to release the contaminant proteins. Then, the column may be regenerated using a solution that will have the effect of releasing most or all proteins from the chromatography medium and reducing or eliminating any microbial contamination that may be present in the chromatography medium. In one embodiment, such a solution may comprise sodium hydroxide. Other reagents can also be used. Subsequently, the column may be rinsed and stored in a solution that can discourage microbial growth. Such a solution may comprise sodium hydroxide, but other reagents can also be appropriate.

The target protein, as well as contaminating proteins that may be present in a sample, can be monitored by any appropriate means. Preferably, the technique should be sensitive enough to detect contaminants in the range between about 2 parts per million (ppm) (calculated as nanograms per milligram of the protein being purified) and 500 ppm. For example, enzyme-linked immunosorbent assay (ELISA), a method well known in the art, may be used to detect contamination of the protein by the second protein. See e.g. Reen (1994), Enzyme-Linked Immunosorbent Assay (ELISA), in *Basic Protein and Peptide Protocols*, Methods Mol. Biol. 32: 461-466, which is incorporated herein by reference in its entirety. In one aspect, contamination of the protein by such other proteins can be reduced after HIC, preferably by at least about two-fold, more preferably by at least about three-fold, more preferably by at least about five-fold, more preferably by at least about ten-fold, more preferably by at least about twenty-fold, more preferably by at least about thirty-fold, more preferably by at least about forty-fold, more preferably by at least about fifty-fold, more preferably by at least about sixty-fold, more preferably by at least about seventy-fold, more preferably by at least about 80-fold, more preferably by at least about 90-fold, and most preferably by at least about 100-fold. In another aspect, contamination of the protein by such other proteins after HIC is not more than about 10,000 ppm, preferably not more than about 2500 ppm, more preferably not more than about 400 ppm, more preferably not more than about 360 ppm, more preferably not more than about 320 ppm, more preferably not more than about 280 ppm, more preferably not more than about 240 ppm, more preferably not more than about 200 ppm, more preferably not more than about 160 ppm, more preferably not more than about 140 ppm, more preferably not more than about 120 ppm, more preferably not more than about 100 ppm, more preferably not more than about 80 ppm, more preferably not more than about 60 ppm, more preferably not more than about 40 ppm, more preferably not more than about 30 ppm, more preferably not more than about 20 ppm, more preferably not more than about 10 ppm, and most preferably not more than about 5 ppm. Such contamination can range from undetectable levels to about 10 ppm or from about 10 ppm to about 10,000 ppm. If a protein is being purified for pharmacological use, one of skill in the art will realize that the preferred level of the second protein can depend on the weekly dose of the protein to be administered per patient, with the aim that the patient will not receive more than a certain amount of a contaminating protein per week. Thus, if the required weekly dose of the protein is decreased, the level of contamination by a second protein may possibly increase.

The amount of DNA that may be present in a sample of the protein being purified can be determined by any suitable method. For example, one can use an assay utilizing polymerase chain reaction. Optionally, the technique can detect DNA contamination at levels of 10 picograms per milligram of protein and greater. DNA levels can be reduced by HIC, optionally by about two-fold, preferably by about five-fold, more preferably by about ten-fold, more preferably by about fifteen-fold, most preferably by about 20-fold. Optionally, levels of DNA after hydroxyapatite chromatography are less than about 20 picograms per milligram of protein, preferably less than 15 picograms per milligram of protein, more preferably less than 10 picograms per milligram of protein, most preferably less than 5 picograms per milligram of protein.

The following examples are intended to illustrate particular embodiments, and not limit the scope, of the invention. Those skilled in the art will readily recognize that additional embodiments are encompassed by the invention.

EXAMPLE 1

Purification of IL1R-II

An HIC flow-through step on Macroprep t-butyl (BioRad Laboratories, Inc.) was employed in purifying a soluble extracellular domain of IL1R-II. A sample containing IL-1R-II was first subjected to purification on a TMAE Fractogel anion-exchange column using 25 mM Tris, pH 8 as the equilibration and wash buffer and 25 mM Tris, 150 mM NaCl, pH 8 as the elution buffer. The HIC step was performed at pH 7.0 with 600 mM citrate in the load buffer. FIG. 1 shows a representative chromatogram of the flow-through step on the t-butyl resin. As can be seen in the figure, a majority (~90% by a quantitative assay) of the loaded protein flows through under these conditions. An elution peak is observed during a wash with 25 mM phosphate, pH 7.0 and a smaller peak was observed in the 0.5N NaOH strip.

Table 1 shows the CHO host cell protein (CHOP) levels in the HIC load, HIC flow-through, and HIC elution fractions from the flow-through purification of IL1R-II shown in FIG. 1. As seen in the table, this step is successful in reducing host cell protein levels by several orders of magnitude. Most of these contaminants tend to bind tightly to the column and come off in the elution peak.

TABLE 1

| Fraction | CHOP levels (ppm) |
| --- | --- |
| HIC load | 12319 |
| HIC flowthrough pool | 974 |
| HIC elution peak | 169199 |

Figure 2:
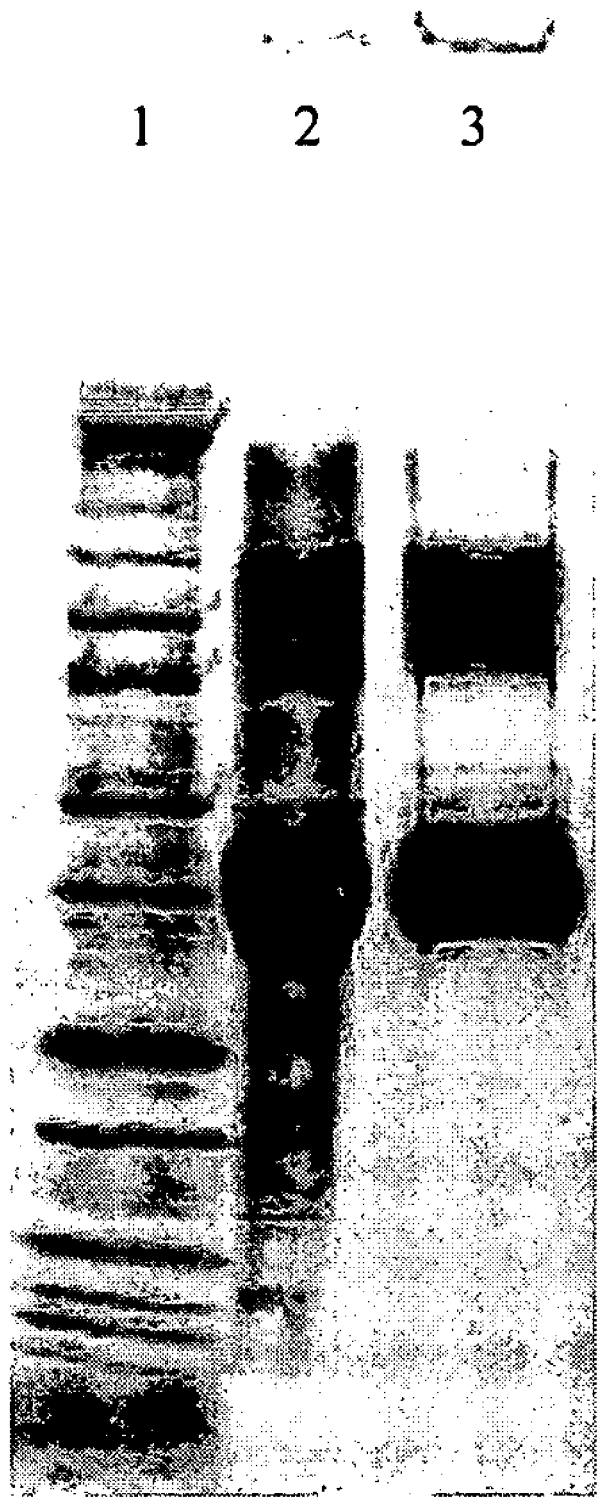

The load and flowthrough fractions were also analyzed by SDS-PAGE. As shown in FIG. 2, the flow-through step on Macroprep t-butyl successfully removed a range of contaminants seen by SDS-PAGE. Lane 1 shows the molecular weight standards, lane two shows a wide distribution of various proteins in the initial sample load, and lane 3 shows that the flow-through fraction eliminated a majority of contaminants to yield a more highly purified form of IL 1R-II (the two bands representing IL1R-II in the form of a monomer and a dimmer).

EXAMPLE 2

Purification of RANK:Fc

The HIC step was employed after the Protein A purification step during downstream processing of RANK:Fc, an Fc fusion protein. At this stage in the process, the predominant impurities in the product include CHOP (~5-10000 ppm), leached protein A (50-200 ppm), high molecular weight aggregate (2-5%) and the peak C form of the protein (5-10%). The peak C form of the protein is potentially misfolded RANK:Fc that has been found to have a lower binding activity than the peak B (main peak) form.

RANK:Fc was purified in an HIC flow-through step using a Macroprep t-butyl resin prepared in accordance with the manufacture's directions. The column was prepared to a capacity of 15 mg/ml at an operating flow rate of 2 cm/min and sanitized with 0.5 NaOH. Following viral inactivation of the Protein A eluate pool, the eluate was diluted with 0.6M citrate solution (pH 6.0, 1:1.75 protein:salt ratio) to raise the final salt concentration of the feed load to 0.4M citrate prior to loading on the column. This level of citrate concentrations were shown to be optimal for separating the product from the impurities listed earlier. Following column equilibration (0.4M citrate, pH 6.0), the feed load containing the RANK:Fc protein was loaded on the column in a buffer consisting of 400 mM Citrate, pH 6.0. The product flowed through, while impurities stayed behind on the column and were removed by a water wash and a 0.5N NaOH regeneration step, followed by sterilization with 0.1M NaOH.

Figure 3:
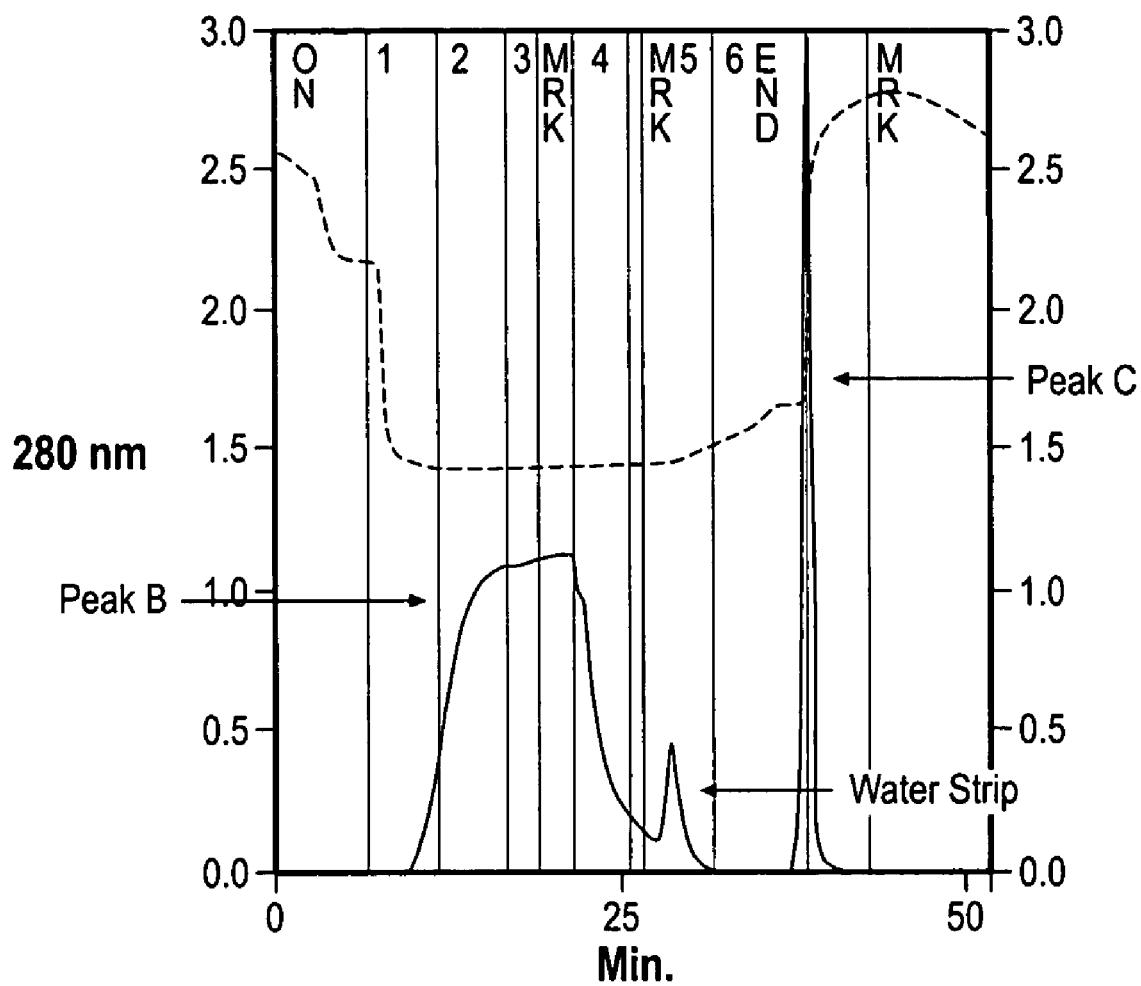
FIG. 3 is a chromatogram showing the purification of RANK:Fc in the flow-through step on a Macroprep t-butyl HIC resin.

The chromatograph shown in FIG. 3 shows the purification of RANK:Fc on a Macroprep t-butyl operated in the flow-through mode. Specifically, the chromatogram shows that the flow-through fraction contained essentially only Peak B (RANK:Fc), while the fractions following elution contained predominantly the other impurities, including CHOP, leached protein A, high molecular weight aggregates and Peak C (the misfolded form of RANK:Fc).

FIG. 4 graphically compares the HIC load to the HIC flow-through pool by various analytical methods including SEC (FIG. 4a), leached Protein A ELISA (FIG. 4b), HIC (FIG. 4c) and fCHOP ELISA (FIG. 4d). Each of these figures indicates that the HIC flow-through step on Macroprep t-butyl is successful in removing aggregates, leached Protein A, the peak C (misfolded) form of the protein and host cell protein contaminants, all in a single step. The extent of clearance of these impurities was found to be far greater than that achieved with a single step on any other non-affinity mode of chromatography for this protein (ion-exchange HIC, metal-chelate etc.).

EXAMPLE 3

Selectivity of Branched Hydrocarbon Functional Groups for Alternate Forms of RANK:Fc A range of HIC support media were compared independently for their selectivity between the peak B and C forms of RANK:Fc as defined by an HIC assay consisting of linear gradient elution (1 to 0M ammonium sulfate) on a TSK Butyl NPR column. Specifically, the chromatography media that were tested included (a) Macroprep t-butyl, (b) TosoHaas Butyl 650M, (c) Butyl Sepharose FF, (d) TosoHaas Phenyl 650M, and (e) TosoHaas Ether 650M. Analytical injections (0.5 mL at a concentration range of 0.5-2 mg/mL of peaks B and C (obtained from a preparative linear gradient experiment on the TSK Butyl NPR analytical column) were loaded onto various HIC columns, and the columns were eluted with a gradient of 400 mM citrate to 0 mM citrate in 15 CV followed by 5 CV washes with water followed by 0.5N NaOH.

Peak B and C forms of the protein were separated by linear salt gradient (from 400 mM citrate to 0 mM citrate at pH 6.0 over 15 column volumes) prior to purification by HIC using the various chromatography media described above. The salt gradient was followed by strip steps with water followed by 0.5N NaOH. HIC using a Macroprep t-butyl column was highly selective, With the peak B being form eluting during the salt gradient (from about 30-50 min) while the peak C form of the protein was very strongly retained and eluting only during the 0.5N NaOH strip step (at about 80 min). In contrast HIC using a TosoHaas Butyl 650M column was much less selective, with both peaks eluting at very close or overlapping intervals during the salt gradient. Similar nonselectivity were observed using Butyl Sepharose 4FF, TosoHaas Phenyl 650M and TosoHaas Ether 650M media. This data indicate that the Macroprep t-butyl resin possesses a unique selectivity for these two similar variants of the same protein. Taken together with the data on the clearance of other impurities, including host cell proteins, leached Protein A and high molecular weight aggregates, this data indicates the utility of the HIC branched alkyl resin as a generic polishing step for a range of proteins produced by cell culture.

While not being bound by any particular theory of mechanistic action, it would appear that these results are due to the unique tertiary butyl functionality present on this resin which is distinct from functionalities on the other resins (linear butyl, phenyl or ether groups). Additionally, it does not appear to be a contribution from the stationary phase backbone, since Macroprep t-butyl, Toso Haas Butyl, Phenyl and Ether resins all share a polymethacrylate backbone.

EXAMPLE 4

Comparison of ter-Butyl and Linear Butyl Resins Having Same Hydrophobicity

HIC resins were prepared with t-butyl and linear butyl functionalities which had similar hydrophobicities in order to determine whether the specificity of the t-butyl resin was attributable to its greater hydrophobicity (relative to the linear butyl resin) or to some specific selectivity associated with the branched physical structure of the t-butyl moiety.

tert-butyl and linear butyl functional groups were immobilized by covalent attachment of their primary amino groups to a commercially available agarose support (NHS-activated Sepharose 4 Fast Flow; Amersham Biosciences, Piscataway, N.J.) via the NHS(N-hydroxysuccinimide) functional moiety, using standard chemistries in accordance with the directions provided by the manufacturer. This linkage forms a very stable amide, especially at high pH. The density of the t-butyl and linear butyl functional groups was adjusted empirically so that the net hydrophobicity of the two resins was equal, as determined by equal retention of RANK:Fc in a gradient of sodium citrate.

Separate Peak B and C forms of the protein were obtained (by linear salt gradient from 400 mM citrate to 0 mM citrate at pH 6.0 over 15 column volumes on a TSK Butyl NPR analytical column) prior to purification by HIC. Analytical injections of the Peak B and C forms (0.5 mL at a concentration range of 0.5-2 mg/mL) were loaded onto the t-butyl and linear butyl columns, prepared as described above, and the columns were eluted with a gradient of 400 mM citrate to 0 mM citrate in 15 column volumes, followed by 5 column volume washes with water, followed by 0.5N NaOH.

The salt gradient was followed by strip steps with water followed by 0.5N NaOH. HIC using the hydrophobically equalized t-butyl column was highly selective, with the peak B form eluting during the salt gradient while the peak C form of the protein was very strongly retained and eluting only during the 0.5N NaOH strip step.

This data indicate that the selectivity of the t-butyl functional group is not due to a difference in hydrophobicity, but rather due to some other property inherent in the branched alkyl structure.

The data on this resin from two different proteins (IL1R-II and RANK:Fc) indicates the generic nature of this flow-through step for purification of proteins, such as recombinantly expressed proteins and recombinantly expressed Fc fusion proteins, and for the removal of such contaminants as CHOP proteins, recombinant protein aggregates, Protein A and misfolded forms of a particular protein.

We claim:

1. A method for separating a target protein from a mixture containing the target protein and non-target protein contaminants, comprising:
    a) contacting the mixture with a hydrophobic adsorbent comprising branched alkyl functional groups having from 4 to about 8 carbon atoms, at least one of which is a tertiary carbon atom, in an aqueous salt solution under loading conditions that permit the non-target protein contaminants to bind to the adsorbent and the target protein to pass through the hydrophobic adsorbent in a flow-through fraction without binding to the hydrophobic adsorbent, wherein the loading condition comprises a pH of from about 5 to about 8.6;
    b) allowing the target protein to pass through the hydrophobic adsorbent in the flow-through fraction portion of the mixture; and
    c) collecting the flow-through fraction portion of the mixture containing the target protein that does not bind to the hydrophobic adsorbent.

2. The method of claim 1, wherein the branched alkyl functional group is tert-butyl.

3. A method for separating a recombinant $F_c$ fusion target protein, produced as a product of cell culture expression in a host cell, from a mixture containing the target protein and non-target protein contaminants, comprising:
    a) contacting the mixture with a hydrophobic adsorbent comprising branched alkyl functional groups having from 4 to about 8 carbon atoms, at least one of which is a tertiary carbon atom, in an aqueous salt solution under loading conditions that permit the non-target protein contaminants to bind to the adsorbent and the target protein to pass through the hydrophobic adsorbent in a flow-through fraction without binding to the hydrophobic adsorbent, wherein the loading condition comprises a pH of from about 5 to about 8.6;
    b) allowing the target protein to pass through the hydrophobic adsorbent in the flow-through fraction portion of the mixture; and
    c) collecting the flow-though fraction portion of the mixture containing the target protein that does not bind to the hydrophobic adsorbent.

4. The method of claim 3, wherein the branched alkyl functional group is tert-butyl.

5. A method for removing Protein A from a mixture containing a target protein and Protein A contaminants, comprising:
    a) contacting the mixture with a hydrophobic adsorbent comprising branched alkyl functional groups having from 4 to about 8 carbon atoms, at least one of which is a tertiary carbon atom, in an aqueous salt solution under loading conditions that permit the Protein A contaminants to bind to the adsorbent and the target protein to pass though the hydrophobic adsorbent in a flow-through fraction without binding to the hydrophobic adsorbent, wherein the loading condition comprises a pH of from about 5 to about 8.6;
    b) allowing the target protein to pass through the hydrophobic adsorbent in the flow-through fraction portion of the mixture; and
    c) collecting the flow-through fraction portion of the mixture containing the target protein that does not bind to the hydrophobic adsorbent.

6. The method of claim 5, wherein the branched alkyl functional group is tert-butyl.

7. A method for removing a misfolded variant of a recombinant target protein from a mixture containing a combination of correctly folded variants and misfolded variants of the target protein, comprising:
    a) contacting the mixture with a hydrophobic adsorbent comprising branched alkyl functional groups having from 4 to about 8 carbon atoms, at least one of which is a tertiary carbon atom, in an aqueous salt solution under loading conditions that permit the misfolded variants of the target protein to bind to the adsorbent and the target protein to pass through the hydrophobic adsorbent in a flow-through fraction without binding to the hydrophobic adsorbent, wherein the loading condition comprises a pH of from about 5 to about 8.6;
    b) allowing the target protein to pass through the hydrophobic adsorbent in the flow-through fraction portion of the mixture; and
    c) collecting the flow-through fraction portion of the mixture containing a correctly folded variant of the target protein that does not bind to the hydrophobic adsorbent.

8. The method of claim 7, wherein the branched alkyl functional group is tert-butyl.

9. A method for removing aggregated forms of a recombinant target protein from a mixture containing individual forms and aggregated forms of the target protein, comprising:
    a) contacting the mixture with a hydrophobic adsorbent comprising branched alkyl functional groups having from 4 to about 8 carbon atoms, at least one of which is a tertiary carbon atom, in an aqueous salt solution under loading conditions that permit the aggregated forms of the target protein to bind to the adsorbent and the target protein to pass through the hydrophobic adsorbent in a flow-through fraction without binding to the hydrophobic adsorbent, wherein the loading condition comprises a pH of from about 5 to about 8.6;

b) allowing the target protein to pass through the hydrophobic adsorbent in the flow-through fraction portion of the mixture; and c) collecting the flow-through fraction portion of the mixture containing the individual form of the target protein that does not bind to the hydrophobic adsorbent.

10. The method of claim 9, wherein the branched alkyl functional group is tert-butyl.

11. A process for separating a recombinant target protein from a mixture containing the target protein and cell culture contaminants produced by cell culture expression of the recombinant protein in a Chinese Hamster Ovary host cell, comprising:

a) contacting the mixture with a hydrophobic adsorbent comprising branched alkyl functional groups having from 4 to about 8 carbon atoms, at least one of which is a tertiary carbon atom, in an aqueous salt solution under loading conditions that permit the cell culture contaminants to bind to the adsorbent and the target protein to pass through the hydrophobic adsorbent in a flow-through fraction without binding to the hydrophobic adsorbent, wherein the loading condition comprises a pH of from about 5 to about 8.6;

b) allowing the target protein to pass through the hydrophobic adsorbent in the flow-through fraction portion of the mixture; and c) collecting the flow-through fraction portion of the mixture containing the target protein that does not bind to the hydrophobic adsorbent.

12. The method of claim 11, wherein the branched alkyl functional group is tert-butyl.

* * * * *

(12) EX PARTE REEXAMINATION CERTIFICATE (9748th)
United States Patent
Shukla et al.

(10) Number: US 7,427,659 C1
(45) Certificate Issued: Jul. 16, 2013

(54) PROCESS FOR PURIFYING PROTEINS IN A HYDROPHOBIC INTERACTION CHROMATOGRAPHY FLOW-THROUGH FRACTION

(75) Inventors: Abhinav A. Shukla, Bellevue, WA (US); Sanchayita Ghose, Newcastle, WA (US)

(73) Assignee: Amgen Inc., Thousand Oaks, CA (US)

Reexamination Request:
No. 90/012,492, Sep. 11, 2012

Reexamination Certificate for:
Patent No.: 7,427,659
Issued: Sep. 23, 2008
Appl. No.: 10/970,860
Filed: Oct. 22, 2004

Related U.S. Application Data

(60) Provisional application No. 60/514,486, filed on Oct. 24, 2003.

(51) Int. Cl.
*C07K 1/00* (2006.01)
*C07K 14/00* (2006.01)

(52) U.S. Cl.
USPC .......... 530/350; 530/344; 530/412; 435/69.1; 435/7.1; 435/183; 435/325

(58) Field of Classification Search
None
See application file for complete search history.

(56) References Cited

To view the complete listing of prior art documents cited during the proceeding for Reexamination Control Number 90/012,492, please refer to the USPTO's public Patent Application Information Retrieval (PAIR) system under the Display References tab.

*Primary Examiner* — Evelyn Huang

(57) ABSTRACT

The present invention is a process for separating a target protein (such as a recombinant protein produced in a cell culture) from a mixture containing the target protein and contaminants (such as cell culture contaminants), by contacting the mixture with a hydrophobic adsorbent comprising branched hydrocarbon functional groups in an aqueous salt solution and collecting the unbound flow-through fraction containing the target protein. In one embodiment, the hydrophobic adsorbent may be a branched alkyl functional group. In another embodiment, the branched alkyl functional group has from 3 to 8 carbon atoms. In another embodiment, the branched alkyl functional group is a tertiary carbon atom, such as tert-butyl.

US 7,427,659 C1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 3, 5, 7, 9 and 11 are determined to be patentable as amended.

Claims 2, 4, 6, 8, 10 and 12, dependent on an amended claim, are determined to be patentable.

New claims 13-21 are added and determined to be patentable.

1. A method for separating a *recombinant* target protein from a mixture containing the *recombinant* target protein and non-target *cell culture* protein contaminants *produced by cell culture expression of the recombinant protein*, comprising:
 a) contacting the mixture *containing a recombinant target protein and a non-target cell culture protein contaminant produced by cell culture expression of the recombinant protein* with a hydrophobic adsorbent comprising branched alkyl functional groups having from 4 to about 8 carbon atoms, at least one of which is a tertiary carbon atom, in an aqueous salt solution under loading conditions that permit the non-target *cell culture* protein contaminants to bind to the adsorbent and the *recombinant* target protein to pass through the hydrophobic adsorbent in a flow-through fraction without binding to the hydrophobic adsorbent, wherein the loading condition comprises a pH of from [about 5] *5.5* to about 8.6;
 b) allowing the *recombinant* target protein to pass through the hydrophobic adsorbent in the flow-through fraction portion of the mixture; and
 c) collecting the flow-through fraction portion of the mixture containing the *recombinant* target protein that does not bind to the hydrophobic adsorbent *to separate the recombinant target protein from the cell culture protein contaminants*.

3. A method for separating a recombinant Fc fusion target protein, produced as a product of cell culture expression in a host cell, from a mixture containing the *recombinant Fc fusion* target protein and non-target protein contaminants, comprising:
 a) contacting the mixture *containing the recombinant Fc fusion target protein and non-target protein contaminants* with a hydrophobic adsorbent comprising branched alkyl functional groups having from 4 to about 8 carbon atoms, at least one of which is a tertiary carbon atom, in an aqueous salt solution under loading conditions that permit the non-target protein contaminants to bind to the adsorbent and the *recombinant Fc fusion* target protein to pass through the hydrophobic adsorbent in a flow-through fraction without binding to the hydrophobic adsorbent, wherein the loading condition comprises a pH of from [about 5] *5.5* to about 8.6;
 b) allowing the *recombinant Fc fusion* target protein to pass through the hydrophobic adsorbent in the flow-through fraction portion of the mixture; and
 c) collecting the flow-through fraction portion of the mixture containing the *recombinant Fc fusion* target protein that does not bind to the hydrophobic adsorbent *to separate the recombinant Fc fusion protein from the non-target protein contaminants*.

5. A method for removing Protein A from a mixture containing [a] *an antibody* target protein and Protein A contaminants, comprising:
 a) contacting the mixture *containing an antibody target protein and Protein A contaminants* with a hydrophobic adsorbent comprising branched alkyl functional groups having from 4 to about 8 carbon atoms, at least one of which is a tertiary carbon atom, in an aqueous salt solution under loading conditions that permit the Protein A contaminants to bind to the adsorbent and the *antibody* target protein to pass though the hydrophobic adsorbent in a flow-through fraction without binding to the hydrophobic adsorbent, wherein the loading condition comprises a pH of from [about 5] *5.5* to about 8.6;
 b) allowing the *antibody* target protein to pass through the hydrophobic adsorbent in the flow-through fraction portion of the mixture; and
 c) collecting the flow-through fraction portion of the mixture containing the *antibody* target protein that does not bind to the hydrophobic adsorbent *to remove Protein A contaminants from the mixture*.

7. A method for removing a misfolded variant of a recombinant target protein from a mixture containing a combination of correctly folded variants and misfolded variants of the *recombinant* target protein, comprising:
 a) contacting the mixture *containing a combination of correctly folded and misfolded variants of the recombinant target protein* with a hydrophobic adsorbent comprising branched alkyl functional groups having from 4 to about 8 carbon atoms, at least one of which is a tertiary carbon atom, in an aqueous salt solution under loading conditions that permit the misfolded variants of the *recombinant* target protein to bind to the adsorbent and the *correctly folded variants of the recombinant* target protein to pass through the hydrophobic adsorbent in a flow-through fraction without binding to the hydrophobic adsorbent, wherein the loading condition comprises a pH of from [about 5] *5.5* to about 8.6;
 b) allowing the *correctly folded variants of the recombinant* target protein to pass through the hydrophobic adsorbent in the flow-through fraction portion of the mixture; and
 c) collecting the flow-through fraction portion of the mixture containing a correctly folded variant of the *recombinant* target protein that does not bind to the hydrophobic adsorbent *to remove the misfolded variant of the recombinant target protein from the mixture*.

9. A method for removing aggregated forms of a recombinant target protein from a mixture containing individual forms and aggregated forms of the *recombinant* target protein, comprising:
 a) contacting the mixture *containing individual and aggregated forms of the recombinant target protein* with a hydrophobic adsorbent comprising branched alkyl functional groups having from 4 to about 8 carbon atoms, at least one of which is a tertiary carbon atom, in an aqueous salt solution under loading conditions that permit the aggregated forms of the target *recombinant* protein to bind to the adsorbent and the *individual form of the* recombinant target protein to pass through the hydrophobic adsorbent in a flow-through fraction without binding to the hydrophobic adsorbent; wherein the loading condition comprises a pH of from [about 5] *5.5* to about 8.6;

b) allowing the *individual form of the recombinant* target protein to pass through the hydrophobic adsorbent in the flow-through fraction portion of the mixture; and c) collecting the flow-through fraction portion of the mixture containing the individual form of the *recombinant* target protein that does not bind to the hydrophobic adsorbent *to remove the aggregated forms of the recombinant target protein from the mixture*.

11. A process for separating a recombinant target protein from a mixture containing the *recombinant* target protein and cell culture contaminants produced by cell culture expression of the recombinant protein in a Chinese Hamster Ovary host cell, comprising:

a) contacting the mixture *containing the recombinant target protein and Chinese Hamster Ovary host cell culture contaminants* with a hydrophobic adsorbent comprising branched alkyl functional groups having from 4 to about 8 carbon atoms, at least one of which is a tertiary carbon atom, in an aqueous salt solution under loading conditions that permit the *Chinese Hamster Ovary host* cell culture contaminants to bind to the adsorbent and the *recombinant* target protein to pass through the hydrophobic adsorbent in a flow-through fraction without binding to the hydrophobic adsorbent, wherein the loading condition comprises a pH of from [about 5] *5.5* to about 8.6;

b) allowing the *recombinant* target protein to pass through the hydrophobic adsorbent in the flow-through fraction portion of the mixture; and c) collecting the flow-through fraction portion of the mixture containing the *recombinant* target protein that does not bind to the hydrophobic adsorbent *to separate the recombinant target protein from the cell culture contaminants*.

13. *The method of claim 1, 3, 7, 9, or 11 wherein the loading condition comprises a pH of from about 6.0 to about 8.6.*

14. *The method of claim 13, wherein the loading condition comprises a pH of from about 6.5 to about 7.5.*

15. *The method of claim 1, 3, 7, 9, or 11, wherein the separation method is further combined with a method of protein purification of the target protein.*

16. *The method of claim 11, wherein the amount of Chinese Hamster Ovary host cell culture contaminants in the flow-through fraction is not more than about 2500 ppm.*

17. *The method of claim 16, wherein the amount of Chinese Hamster Ovary host cell culture contaminants in the flow-through fraction is not more than about 400 ppm.*

18. *The method of claim 11, wherein the amount of Chinese Hamster Ovary host cell culture contaminants in the flow-through fraction is not more than about 100 ppm.*

19. *The method of claim 11, wherein the cell culture contaminants are selected from the group of a recombinant target protein aggregate, a misfolded recombinant target protein, and mixtures thereof.*

20. *The method of claim 7, wherein the recombinant target protein is a Fc fusion protein.*

21. *The method of claim 20, wherein the Fc fusion protein is selected from the group consisting of receptor activator of NF-kappa B:Fc (RANK:Fc) and human p75 tumor necrosis factor receptor:Fc (p75 TNFR:Fc).*

\* \* \* \* \*